United States Patent [19]

Schmucker et al.

[11] Patent Number: 5,318,778
[45] Date of Patent: Jun. 7, 1994

[54] DEODORIZING LANTIBIOTIC COSMETIC AGENTS

[75] Inventors: Robert Schmucker, Hamburg; Sauermann, Gerhard, Wiemersdorf; Ulrich Eigener, Hamburg; Walter Engel, Pinneberg, all of Fed. Rep. of Germany

[73] Assignee: Beiersdorf AG, Hamburg, Fed. Rep. of Germany

[21] Appl. No.: 852,151

[22] PCT Filed: Nov. 2, 1990

[86] PCT No.: PCT/DE90/00837

§ 371 Date: Mar. 31, 1992

§ 102(e) Date: Mar. 31, 1992

[87] PCT Pub. No.: WO91/07164

PCT Pub. Date: May 30, 1991

[30] Foreign Application Priority Data

Nov. 16, 1989 [DE] Fed. Rep. of Germany ....... 3938140

[51] Int. Cl.$^5$ .......................... A61K 7/32; A61K 9/10; A61K 9/14; A61K 37/02

[52] U.S. Cl. .................................. 424/401; 424/46; 424/47; 424/65; 424/489; 424/DIG. 5; 424/70; 514/2; 514/769; 514/772; 514/12

[58] Field of Search ....................... 424/489, 46, 47, 65, 424/70, 401; 514/2

[56] References Cited

U.S. PATENT DOCUMENTS

| | | | |
|---|---|---|---|
| 4,871,539 | 10/1989 | Hata et al. | 435/853 |
| 4,980,163 | 12/1990 | Blackburn et al. | 514/12 |
| 4,996,055 | 2/1991 | Kurasawa | 424/442 |
| 5,135,910 | 8/1992 | Blackburn et al. | 514/2 |

FOREIGN PATENT DOCUMENTS 342486  11/1989  European Pat. Off. .

*Primary Examiner*—Thurman K. Page
*Assistant Examiner*—James M. Spear
*Attorney, Agent, or Firm*—Sprung Horn Kramer & Woods

[57] ABSTRACT

Cosmetic deodorants, characterized by an effective content of lantibiotics, it being possible for the lantibiotics to be present both singly and in a mixture.

24 Claims, No Drawings

DEODORIZING LANTIBIOTIC COSMETIC AGENTS

The present invention relates to cosmetic deodorants. Such formulations are used to eliminate body odour which is formed when fresh perspiration, which is odourless per se, is decomposed by microorganisms. The commercial cosmetic deodorants are based on different active principles.

The formation of perspiration can be suppressed by astringents—predominantly aluminum salts such as aluminum hydroxychloride. Apart from the denaturation of the skin proteins, however, the substances used for this purpose interfere drastically in the heat regulation of the axillary region and should at best [lacuna] be used in exceptional cases.

The bacterial flora on the skin can be reduced by antimicrobial substances. Ideally here, only the odour-causing microorganisms should be destroyed. In practice, however, it turns out that the entire microflora of the skin are damaged to the same extent. Occasionally, even the microorganisms which cause no odour are relatively severely damaged.

Finally, body odour can also be concealed by fragrances, the classical method, which, however, is the least able to meet the aesthetic needs of the consumer, as the mixture of body odour and perfume fragrance smells rather unpleasant.

Deodorants should fulfill the following conditions:
1) The biological processes of the skin must not be impaired.
2) The deodorants should have no distinct intrinsic odour.
3) They must be harmless in the case of overdosage or other unintended use.
4) They should not concentrate on the skin after repeated use.
5) It should be possible to incorporate them easily into commercial cosmetic formulations.

Those which are known and usable are both liquid deodorants, for example aerosol sprays, roll-ohs and the like and solid preparations, for example deodorant sticks, powders, powder sprays, intimate cleansers etc.

It was the aim of the present invention to develop cosmetic deodorants which do not have the disadvantages of the prior art. In particular, the deodorants should largely spare the microflora of the skin, but selectively reduce the microorganisms which are responsible for body odour.

It has been found, and in this the object is achieved, that cosmetic deodorants having an effective content of lantibiotics remedy the disadvantages of the prior art.

Lantibiotics have been known for many years. They are polypeptides which are synthesized by microorganisms and are distinguished by the presence of lanthionine in the peptide sequence.

The lanthionines have the following structures:

$$HOOC-CH(NH_2)-CH_2-S-CH_2-CH(NH_2)-COOH$$

written in another way:

$$H_2N-ala-S-ala-COOH \quad \text{(meso-lanthionine)}$$
[lacuna]
COOH NH$_2$ and $$HOOC-CH(NH_2)-CH_2-S-CH(CH_3)-CH(NH_2)-COOH$$

written in another way:

$$H_2N-ala-S-aba-COOH \quad \text{(threo-methyl-lanthionine)}$$
[lacuna]
COOH NH$_2$ In the lantibiotics, ring structures are formed using these lanthionines.

Examples of lantibiotics are nisin, epidermin, subtilin, cinramycin, duramycin, ancovenin, gallidermin and Pep 5.

The abovementioned substances are known per se and can be found under the Chemical Abstracts registry numbers:

| | |
|---|---|
| Nisin | 1414-45-5 |
| Epidermin | 99165-17-0 |
| Subtilin | 1393-38-0 |
| Pep 5 | 110655-58-8 |
| Duramycin | 1391-36-2 |
| Ancovenin | 88201-41-6 |
| Gallidermin | 117978-77-5 |

Nisin, for example, is a peptide composed of 34 amino acids, which is synthesized by Streptococcus lactis. It acts predominantly against micrococci and coryneforn bacteria. In some countries it is an antibiotic permitted as a foodstuff preservative (not in Germany).

Nisin has the following amino acid sequence (primary structure):

H$_2$N—ile—dhb—ala—ile—dha—leu—ala—aba—pro—gly—ala—lys—
—aba—gly—ala—leu—met—gly—ala—asn—
—met—lys—aba—ala—aba—ala—his—ala—
—ser—ile—his—val—dha—lys—COOH (with S—S bridges as shown)

where
dhb is dehydrobutyrin
dha is dehydroalanine
aba is aminobutyric acid.

E. Gross, J.L. Morell, "The Structure of Nisin", J. Amer. Chem. Soc. 93, pp. 4634–4637 (1971).

The mechanism of action of nisin and of the lantibiotics related to nisin and having substantially the same action can be interpreted as follows: cell walls are destroyed as a result of release of autolysins. As channels are additionally formed in the cytoplasmic membrane, low molecular weight cell constituents can diffuse out, as a result of which the (prokaryotic) cell is destroyed.

The correctness of this interpretation is, however, of no importance for the invention. It is only meant as an attempt to illustrate the microbiological processes.

Eukaryotic cells, i.e. skin cells, fungi etc, are resistant to nisin and other lantibiotics.

Lantibiotics are virtually non-toxic to mammals. The LD50 for nisin, for example, is greater than 7 g/kg (determined for rats and cats).

Investigations of the suitability of antibiotics as deodorants are described in "Seifen-Öle-Fette-Wachse", Vol. 97, No. 16, 5 Aug. 1981, Ing. Chem. H. Bartl: "Kosmetik-Rohstoffe, Antibiotika als Deodorantien", pages 556-557. Quoted are penicillin, streptomycin, neomycin, that is to say broad-spectrum antibiotics capable of ruining the harmless microflora too. However, it is the intention of the invention to spare these. In the footnote (loc. cit. page 556 foot) reference is then also made to the recommendation that the use of antibiotics in the manufacture of cosmetic products be dispensed with. Furthermore, the cited antibiotics belong to classes of structure which have nothing in common with lantibiotics.

EP-A-0 342 486 describes the use of gallidermin in medicaments active against certain pathogens, for example associated with skin diseases. Claim 9 of this specification admittedly relates verbally to a cosmetic agent containing gallidermin, that is to say a representative of the lantibiotics. However, the disclosure in this specification does not allow any inferences about a use in deodorizing cosmetics. Mention is made simply and solely of the use of gallidermin as agent against acne, a disorder which causes great psychological stress to those affected and which can be regarded as a cosmetic problem only in the widest possible sense.

It was surprising and unforeseeable for the person skilled in the art that cosmetic compositions containing lantibiotics according to the present invention
- would be stable on storage
- would have a sufficiently high half life on the skin
- would be suitable for use as a cosmetic
- would be selectively active against odour-producing
- microorganisms
- would spare the symbiontic (sic) microflora of the skin.

It was in particular surprising that the compositions according to the invention are not only suitable for cosmetic purposes, but are moreover more effective and milder than the compositions of the prior art.

It turns out that lantibiotics can be successfully incorporated into all the usual types of deodorant formulations.

The lantibiotics are preferably present in concentrations of 0.1-10,000 ppm. The lantibiotics are particularly preferably present in concentrations of 0.1-750 ppm, very particularly preferably in concentrations of 0.5-400 ppm. The concentration data in each case relate to the content of pure active compound and to the total weight of the composition.

Formulations having an effective content of nisin, epidermin and/or gallidermin have turned out to be particularly advantageous. However, the other lantibiotics mentioned are also highly suitable for use according to the invention.

It is possible and possibly advantageous to employ a mixture of lantibiotics as the effective principle of the compositions according to the invention.

It is advantageous to buffer the compositions according to the invention in a pH range from 2.5-6.5. It is particularly favourable to choose the pH in a range from 3.5-4.8.

It can additionally be advantageous to incorporate additives into the compositions which increase the stability of the lantibiotics, for example, preservatives, antioxidants, other proteins, photostabilizers etc.

Otherwise, the customary measures for the composition of cosmetic formulations, which are known to the person skilled in the art, are to be observed.

The lantibiotics can be incorporated into the compositions according to the invention in a simple manner. They are preferably added in dissolved for (for example as an aqueous, alcoholic or alcoholic-aqueous solution) to the other components of the formulations. However, it is very particularly advantageous to incorporate lantibiotics into so-called powder sprays. It is also advantageous to avoid additives which can damage the natural microflora, as the lantibiotics in themselves selectively reduce the odour-producing microorganisms.

If it is intended to incorporate lantibiotics in powder sprays, the suspension bases for these can advantageously be chosen from the group comprising aerosil, magnesium carbonate, magnesium oxide, kieselguhr, kaolin, talc, modified starch, metal soaps (for example zinc stearate), titanium dioxide, aluminum oxide, calcium carbonate, zinc oxide, silk powder, nylon powder, polyethylene powder and related substances.

The following examples are used to describe the invention without it being intended to restrict the invention to these examples.

| Example 1 | |
|---|---|
| Pump spray | |
| Nisin (pure substance) | 0.025 g |
| Ethanol, pharm. (96%) | 354.875 g |
| Perfume, colorant | according to choice |
| Water | to 1,000.000 g |
| Example 2 | |
| Pump spray | |
| Epidermin | 0.010 g |
| Ethanol, pharm. (96%) | 354.875 g |
| Perfume, colorant | according to choice |
| Water | to 1,000.000 g |
| Example 3 | |
| Deodorant roller (roll-on) | |
| Nisin | 0.150 g |
| Hydroxyethylcellulose | 5.000 g |
| Propylene glycol | 5.000 g |
| Ethanol, pharm. (96%) | 355.850 g |
| Perfume, colorant | according to choice |
| Water | to 1,000.000 g |
| Example 4 | |
| Deodorant roller (roll-on) | |
| Epidermin | 0.120 g |
| Hydroxyethylcellulose | 5.000 g |
| Propylene glycol | 5.000 g |
| Ethanol, pharm. (96%) | 355.850 g |
| Perfume, colorant | according to choice |
| Water | to 1,000.000 g |
| Example 5 | |
| Spray | |
| Nisin | 0.200 g |
| Ethanol, pharm. (96%) | 150.000 g |
| Propylene glycol | 50.000 g |
| Dimethyl ether | 300.000 g |
| Perfume | according to choice |

-continued

| | |
|---|---|
| Water | to 1,000.000 g |
| Example 6 | |
| Spray | |
| Epidermin | 0.150 g |
| Ethanol, pharm. (96%) | 150.000 g |
| Propylene glycol | 50.000 g |
| Dimethyl ether | 300.000 g |
| Perfume | according to choice |
| Water | to 1,000.000 g |
| Example 7 | |
| Spray | |
| Nisin | 0.180 g |
| Ethanol, pharm. (96%) | 497.160 g |
| 2-Octyldodecanol | 2.660 g |
| Perfume | according to choice |
| Dimethyl ether | to 1,000.000 g |
| Example 8 | |
| Spray | |
| Epidermin | 0.150 g |
| Ethanol, pharm. (96%) | 497.160 g |
| 2-Octyldodecanol | 2.660 g |
| Perfume | according to choice |
| Dimethyl ether | to 1,000.000 g |
| Example 9 | |
| Nisin | 1.200 g |
| Cetylstearyl alcohol | 20.000 g |
| 2-Octyldodecanol | 20.000 g |
| Kaolin | 200.200 g |
| Talc | 200.200 g |
| Aerosil | 48.200 g |
| Perfume | according to choice |
| Rice starch | to 1,000.000 g |
| Example 10 | |
| Epidermin | 1.000 g |
| Cetylstearyl alcohol | 20.000 g |
| 2-Octyldodecanol | 20.000 g |
| Kaolin | 200.200 g |
| Talc | 200.200 g |
| Aerosil | 48.200 g |
| Perfume | according to choice |
| Rice starch | to 1,000.000 g |
| Example 11 | |
| Washing gel concentrate | |
| Nisin | 9.000 g |
| Cocoamidopropylbetaine | 613.300 g |
| Tipa lauryl ether sulphate | 306.700 g |
| Sodium chloride | according to choice |
| Perfume, colorant | according to choice |
| Citric acid | 1.000 g |
| Glycerol | 10.000 g |
| Water | to 1,000.00 g [sic] |
| Example 12 | |
| Washing gel concentrate | |
| Epidermin | 7.000 g |
| Cocoamidopropylbetaine | 613.300 g |
| Tipa lauryl ether sulphate | 306.700 g |
| Sodium chloride | according to choice |
| Perfume, colorant | according to choice |
| Citric acid | 1.000 g |
| Glycerol | 10.000 g |
| Water | to 1,000.00 g [sic] |
| Example 13 | |
| Powder spray I | |
| a) Suspension base | |
| Polymethylsiloxane (cyclomethicone) | 72.000 g |
| Talc | 24.000 g |
| Bentonite gel IPM | 3.000 g |
| Nisin | 1.000 g |
| b) Ready-to-use spray | |
| Suspension base I | 20.000 g |
| Propane/butane | 80.000 g |
| Example 14 | |
| Powder spray II | |
| a) Suspension base | |
| Polymethylsiloxane (cyclomethicone) | 72.000 g |
| Titanium dioxide | 24.000 g |
| Bentonite gel IPM | 3.000 g |
| Nisin | 1.000 g |

-continued

| | |
|---|---|
| b) Ready-to-use spray | |
| Suspension base I | 20.000 g |
| Propane/butane | 80.000 g |
| Example 15 | |
| Powder spray III | |
| a) Suspension base | |
| Polymethylsiloxane (cyclomethicone) | 72.000 g |
| Silk powder | 24.000 g |
| Bentonite gel IPM | 3.000 g |
| Nisin | 1.000 g |
| b) Ready-to-use spray | |
| Suspension base I | 20.000 g |
| Propane/butane | 80.000 g |

The compositions according to Examples 1–15 were evaluated by the so-called sniff test.

Compositions according to the invention were tested against placebos i.e. compositions identical except for the content of active substance. A group of 40 subjects had the duty of in each case treating one armpit with composition according to the invention and the other with placebo. The subjects then wore a shirt with panty liners under the armpits for three hours. After this period had expired, the panty liners were transferred to separate flasks. The odour of the liners was evaluated by three test persons. The test was carried out as a double-blind test so that neither the subjects nor the test persons knew which armpit had been treated with which composition.

It turned out that the preparations containing active compound in each case acted better than the corresponding placebos in 38 of the 40 cases subjected to sensory evaluation. In 2 of the 40 cases, the test persons indicated that treated and untreated samples could not be differentiated from one another.

We claim:

1. A cosmetic deodorant consisting essentially of a cosmetic base and a lantibiotic.

2. A deodorant according to claim 1, wherein the lantibiotic consists essentially of at least one member selected from the group consisting of nisin, epidermin, subtilin, cinramycin, duramycin, ancovenin, Pep 5 and gallidermin.

3. A deodorant according to claim 1, wherein the lantibiotic is present in from 0.1 to 10,000 ppm.

4. A deodorant according to claim 1, wherein the lantibiotic is present in from 0.1 to 750 ppm.

5. A deodorant according to claim 1, wherein the lantibiotic is present in from 0.5 to 400 ppm.

6. A deodorant according to claim 1, buffered to be acidic.

7. A deodorant according to claim 1, buffered to a pH from 2.5 to 6.5.

8. A deodorant according to claim 1, buffered to a pH from 3.5 to 4.8.

9. A deodorant according to claim 1, in the form of a deodorant spray, deodorant roll-on, deodorant pump spray, deodorizing intimate cleanser, deodorizing shampoo, deodorizing shower or bath preparation, deodorizing powder, deodorizing powder spray or deodorant stick.

10. A method of deodorizing the skin of an individual which comprises applying to the skin of such individual a deodorizing amount of a deodorant according to claim 1.

11. A deodorant according to claim 1, in the form of an aqueous, alcoholic or aqueous-alcoholic solution or dispersion containing the lantibiotic.

12. A deodorant according to claim 11, in the form of a spray, a pump spray or a powder spray.

13. A deodorant according to claim 12, in the form of a powder spray containing a suspension base, said suspension base being selected from the group consisting of aerosol, talc, modified starch, a metal soap, zinc oxide, silk powder, nylon powder and polyethylene powder.

14. A deodorant according to claim 11, in the form of a roll on composition.

15. A deodorant according to claim 11, in the form of a washing gel concentrate.

16. A deodorant according to claim 1, in the form of a spray and further containing ethanol, a perfume, and at least one of water and dimethyl ether.

17. A deodorant according to claim 1, in the form of a roll on composition further containing water, ethanol, propylene glycol, hydroxyethylcellulose and a perfume.

18. A deodorant according to claim 16, containing dimethyl ether and further containing propylene glycol.

19. A deodorant according to claim 16, further containing 2-octyldodecanol.

20. A deodorant according to claim 1, in the form of a powder and further containing cetylstearyl alcohol, 2-octyldodecanol, kaolin, talc, aerosol, rice starch and a perfume.

21. A deodorant according to claim 11, in the form of a washing gel concentrate and further containing cocoamidopropylbetaine, tipa lauryl ether sulphate, glycerol and water.

22. A deodorant according to claim 11, in the form of a powder spray and further containing polymethylsiloxane, talc and at least one of propane and butane.

23. A method of cosmetically deodorizing the skin of a person which comprises applying thereto a composition according to claim 1.

24. A method of cosmetically deodorizing the skin of a person which comprises applying thereto a composition according to claim 11.

* * * * *